US012588876B2

(12) United States Patent
Chen et al.

(10) Patent No.: US 12,588,876 B2
(45) Date of Patent: Mar. 31, 2026

(54) TARGET AREA DETERMINATION METHOD AND MEDICAL IMAGING SYSTEM

(71) Applicant: GE Precision Healthcare LLC, Wauwatosa, WI (US)

(72) Inventors: Fuqiang Chen, Beijing (CN); Xihui Ju, Beijing (CN); Hankun Xue, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 539 days.

(21) Appl. No.: 17/828,545

(22) Filed: May 31, 2022

(65) Prior Publication Data

US 2022/0378383 A1 Dec. 1, 2022

(30) Foreign Application Priority Data

May 31, 2021 (CN) .......................... 202110600001.X

(51) Int. Cl.
 *A61B 6/03* (2006.01)
 *G06T 7/00* (2017.01)
 *G16H 30/40* (2018.01)
(52) U.S. Cl.
 CPC ........... *A61B 6/032* (2013.01); *G06T 7/0012* (2013.01); *G16H 30/40* (2018.01); *G06T 2207/10081* (2013.01); *G06T 2207/30004* (2013.01)
(58) Field of Classification Search
 CPC .................. A61B 6/032; G06T 7/0012; G06T 2207/10081; G06T 2207/30004; G06T 7/0014; G06T 5/80; G06T 7/73; G06T 11/003; G06T 11/40; G16H 30/40; G16H 50/20; G16H 50/70
(Continued)

(56) References Cited

U.S. PATENT DOCUMENTS

2014/0022253 A1* 1/2014 Nakagawa .............. G06T 19/20
                                                  345/427
2015/0185302 A1* 7/2015 Nitta .................... G01R 33/546
                                                  324/318
(Continued)

OTHER PUBLICATIONS

Automatic Marker-free Longitudinal Infrared Image Registration by Shape Context Based Matching and Competitive Winner-guided Optimal Corresponding, by Lee, Chia-Yen, Wang, Hao-Jen, Lai, Jhih-Hao, Chang, Yeun-Chung, Huang, Chiun-Sheng, Pub. Scientific Reports, 7, 39834, Pub: Feb. 1, 2017 (Year: 2017).*
(Continued)

*Primary Examiner* — Jennifer Mehmood
*Assistant Examiner* — Heath E. Wells

(57) ABSTRACT

Provided in the present application are a target area determination method and a medical imaging system, specifically a target area determination method and device, a medical imaging system, and a non-transitory computer-readable storage medium. The target area determination method includes: pre-processing an original image to acquire a pre-processed medical image, acquiring a target point in the medical image, and acquiring a plurality of sectional images of the medical image according to the target point, and acquiring, on the basis of a first model, a target area corresponding to the target point in the plurality of sectional images.

12 Claims, 8 Drawing Sheets

430

420

410

(58) Field of Classification Search
USPC ............................................................ 382/131
See application file for complete search history.

(56) References Cited

U.S. PATENT DOCUMENTS

| | | | | |
|---|---|---|---|---|
| 2015/0209015 | A1* | 7/2015 | Oh | A61B 8/463 |
| | | | | 600/443 |
| 2015/0371361 | A1* | 12/2015 | Kim | G06T 7/74 |
| | | | | 382/128 |
| 2018/0353148 | A1* | 12/2018 | Smith | G06T 7/11 |
| 2020/0008875 | A1* | 1/2020 | Lu | A61N 5/1039 |
| 2020/0074712 | A1* | 3/2020 | Wu | G06T 3/60 |
| 2020/0273160 | A1* | 8/2020 | Zhang | G16H 30/40 |
| 2021/0264613 | A1* | 8/2021 | Wang | G06V 10/774 |
| 2021/0350544 | A1* | 11/2021 | Renisch | G06T 7/149 |
| 2022/0245756 | A1* | 8/2022 | Mulford | G06T 3/10 |
| 2022/0301224 | A1* | 9/2022 | Zhang | G06T 7/75 |

OTHER PUBLICATIONS

Alkadi et al., "A 2.5D Deep Learning-Based Approach for Prostate Cancer Detection on T2-Weighted Magnetic Resonance Imaging." In: Leal-Taixé, L., Roth, S. (eds) Computer Vision—ECCV 2018 Workshops. ECCV 2018. Lecture Notes in Computer Science(), vol. 11132. Springer, Cham. https://doi.org/10.1007/978-3-030-11018-5_66, 6 pages.

* cited by examiner

Pre-processing module

110

Target point acquisition module

120

Area determination module

130

100

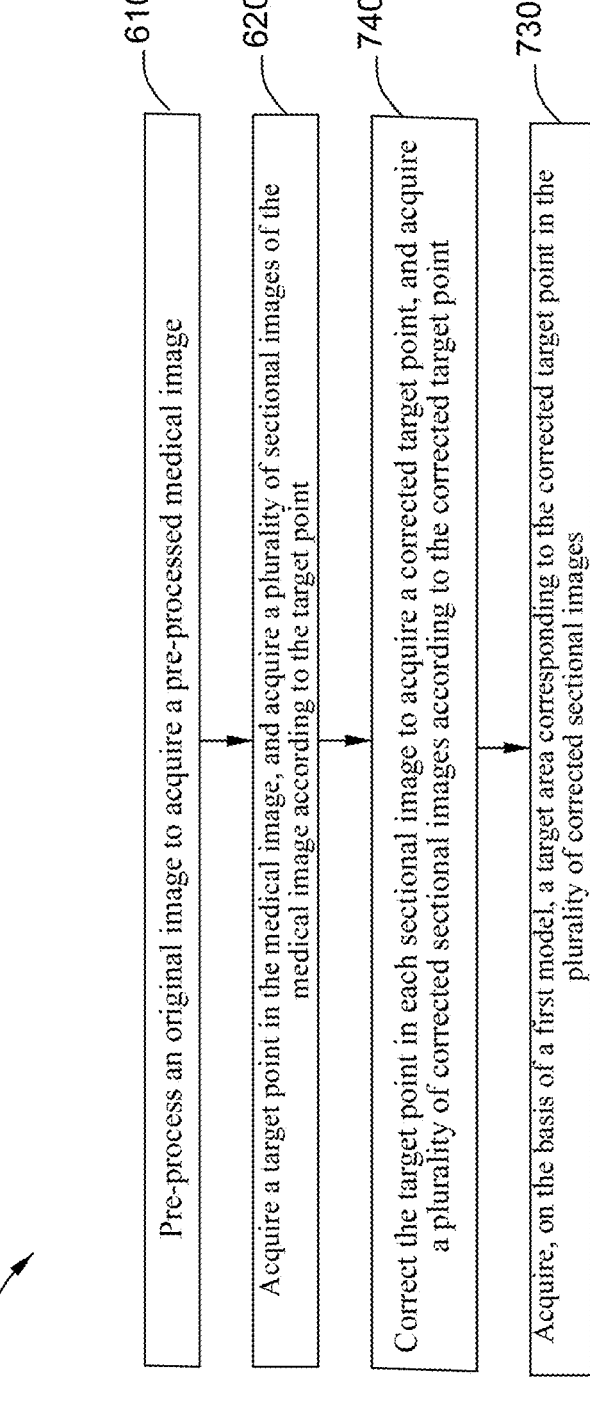

700

610 — Pre-process an original image to acquire a pre-processed medical image

620 — Acquire a target point in the medical image, and acquire a plurality of sectional images of the medical image according to the target point 740 — Correct the target point in each sectional image to acquire a corrected target point, and acquire a plurality of corrected sectional images according to the corrected target point 730 — Acquire, on the basis of a first model, a target area corresponding to the corrected target point in the plurality of corrected sectional images

TARGET AREA DETERMINATION METHOD AND MEDICAL IMAGING SYSTEM

CROSS-REFERENCE TO RELATED APPLICATIONS

This application claims priority to Chinese Patent Application No. 202110600001.X, filed on May 31, 2021, the disclosure of which is incorporated herein by reference in its entirety.

TECHNICAL FIELD

The present disclosure relates to medical image processing, in particular to a target area determination method, a medical imaging system, and a non-transitory computer-readable storage medium.

BACKGROUND

In computed tomography (CT) processing, a detector is used to acquire data of X-rays after passing through a subject under examination, and then the acquired X-ray data is processed to obtain projection data. Such projection data can be used to reconstruct a CT image. Complete projection data can be used to reconstruct an accurate CT image for diagnosis.

Typically, after a CT image is acquired, the CT image needs to be segmented to acquire an image of a target area for further use in disease diagnosis. For example, first, an image of a heart area needs to be acquired from the CT image by means of segmentation, and then the image of the heart area is further processed or subjected to computation for diagnosis of coronary stenosis.

In the process of acquiring the image of the heart area, processing is usually performed on the basis of 3D data. However, processing of the 3D data requires a large number of image sets and results in a heavy computation load. However, a large amount of information will be lost if 2D data is used.

SUMMARY

The present disclosure provides a target area determination method, a medical imaging system, and a non-transitory computer-readable storage medium.

Provided in an exemplary embodiment of the present disclosure is a target area determination method, including pre-processing an original image to acquire a pre-processed medical image, acquiring a target point in the medical image, and acquiring a plurality of sectional images of the medical image according to the target point, and acquiring, on the basis of a first model, a target area corresponding to the target point in the plurality of sectional images.

Specifically, the pre-processing comprises at least one of resizing and pixel padding.

Specifically, the target point in the medical image is a location center point of the original image.

Specifically, the plurality of sectional images include a transverse plane image, a coronal plane image and a sagittal plane image.

Specifically, training data of the first model includes a first data set and a second data set. The first data set includes a plurality of sectional images having a preset target point. The second data set includes distances from the preset target point to respective edges of a reference target area in each sectional image. The preset target point includes an initial target point or an offset target point. The initial target point is the location center point of the original image. The offset target point is a target point having a preset offset from a reference target point. The reference target point is the center of the reference target area.

Specifically, the acquiring the target area corresponding to the target point in the plurality of sectional images includes inputting the plurality of sectional images containing the target point into the first model, and outputting distances from the target point to respective edges of a reference target area in each sectional image, and acquiring the target area on the basis of the distances.

Specifically, the method further includes correcting the target point in each sectional image to acquire a corrected target point, and acquiring a plurality of corrected sectional images according to the corrected target point. Acquiring the target area corresponding to the target point in the plurality of sectional images includes acquiring a target area corresponding to the corrected target point in the plurality of corrected sectional images.

Specifically, correcting the target point in each sectional image includes acquiring the corrected target point on the basis of a second model.

Specifically, training data of the second model includes a third data set and a fourth data set. The third data set includes a plurality of sectional images having an initial target point. The fourth data set includes an offset between the initial target point and a reference target point in each sectional image. The initial target point is the location center point of the original image. The reference target point is the center of the reference target area.

Further provided in an exemplary embodiment of the present disclosure is a non-transitory computer-readable storage medium for storing a computer program, wherein the computer program, when executed by a computer, causes the computer to execute instructions for the target area determination method.

Further provided in an exemplary embodiment of the present disclosure is a medical imaging system including a processor used to perform the target area determination method.

Further provided in an exemplary embodiment of the present disclosure is a medical imaging system including a target area determination device including a pre-processing module, a target point acquisition module, and an area determination module The pre-processing module is configured to pre-process an original image to acquire a pre-processed medical image, the target point acquisition module is configured to acquire a target point in the medical image and to acquire a plurality of sectional images of the medical image according to the target point, and the area determination module is configured to acquire, on the basis of a first model, a target area corresponding to the target point in the plurality of sectional images.

Specifically, the target point in the medical image is a location center point of the original image.

Specifically, the pre-processing includes at least one of resizing and pixel padding.

Specifically, the plurality of sectional images include a transverse plane image, a coronal plane image, and a sagittal plane image.

Specifically, training data of the first model includes a first data set and a second data set. The first data set includes a plurality of sectional images having a preset target point. The second data set includes distances from the preset target point to respective edges of a reference target area in each sectional image. The preset target point incudes an initial target point or an offset target point. The initial target point is the location center point of the original image. The offset target point is a target point having a preset offset from a reference target point. The reference target point is the center of the reference target area.

Specifically, the area determination module is further configured to input the plurality of sectional images including the target point into the first model and output distances from the target point to respective edges of a reference target area in each sectional image, and to acquire the target area on the basis of the distances.

Specifically, the target area determination device further includes a target point correction module, configured to correct the target point in each sectional image to acquire a corrected target point, and to acquire a plurality of corrected sectional images according to the corrected target point. The area determination module is configured to acquire the target area corresponding to the corrected target point in the plurality of corrected sectional images.

Specifically, the target point correction module is further configured to acquire the corrected target point on the basis of a second model.

Specifically, training data of the second model includes a third data set and a fourth data set. The third data set includes a plurality of sectional images having an initial target point. The fourth data set includes an offset between the initial target point and a reference target point in each sectional image. The initial target point is the location center point of the original image. The reference target point is the center of the reference target area.

Other features and aspects will become apparent from the following detailed description, accompanying drawings, and claims.

BRIEF DESCRIPTION OF THE DRAWINGS

The present disclosure can be better understood through the description of exemplary embodiments of the present disclosure in conjunction with the accompanying drawings, in which:

FIG. 8 is a flowchart of a target area determination method according to some other embodiments of the present disclosure.

DETAILED DESCRIPTION

Specific implementations of the present disclosure will be described below. It should be noted that in the specific description of these embodiments, for the sake of brevity and conciseness, this specification may not describe all features of the actual implementations in detail. It should be understood that in the actual implementation process of any implementations, just as in the process of any engineering project or design project, a variety of specific decisions are often made to achieve specific goals of the developer and to meet system-related or business-related constraints, which may also vary from one implementation to another. Furthermore, it should also be understood that although efforts made in such development processes may be complex and tedious, for those of ordinary skill in the art related to the content disclosed in the present disclosure, some design, manufacture or production changes on the basis of the technical content disclosed in the present disclosure are only common technical means, and should not be construed as insufficient content of the present disclosure.

Unless defined otherwise, technical terms or scientific terms used in the claims and specification should have usual meanings understood by those of ordinary skill in the technical field to which the present disclosure belongs. The terms "first," "second," and similar terms used in the description and claims of the patent application of the present disclosure do not denote any order, quantity, or importance, but are merely intended to distinguish between different constituents. The terms "one" or "a/an" and similar terms do not denote a limitation of quantity, but rather the presence of at least one. The terms "include" or "comprise" and similar terms mean that an element or article in front of "include" or "comprise" encompass elements or articles and their equivalent elements listed after "include" or "comprise", and do not exclude other elements or articles. The term "connect" or "connected" and similar words are not limited to physical or mechanical connections, and are not limited to direct or indirect connections.

As used in the present disclosure, the term "the subject under examination" may include any object being imaged.

It should be noted that from the perspective of those of ordinary skill in the art or related art, such description should not be construed as limiting the present disclosure only to a CT system. In fact, the target area determination method and device described here may be reasonably applied to other imaging fields in medical fields or non-medical fields, such as X-ray systems, PET systems, SPECT systems, MR systems, or any combination thereof.

Figure 1:
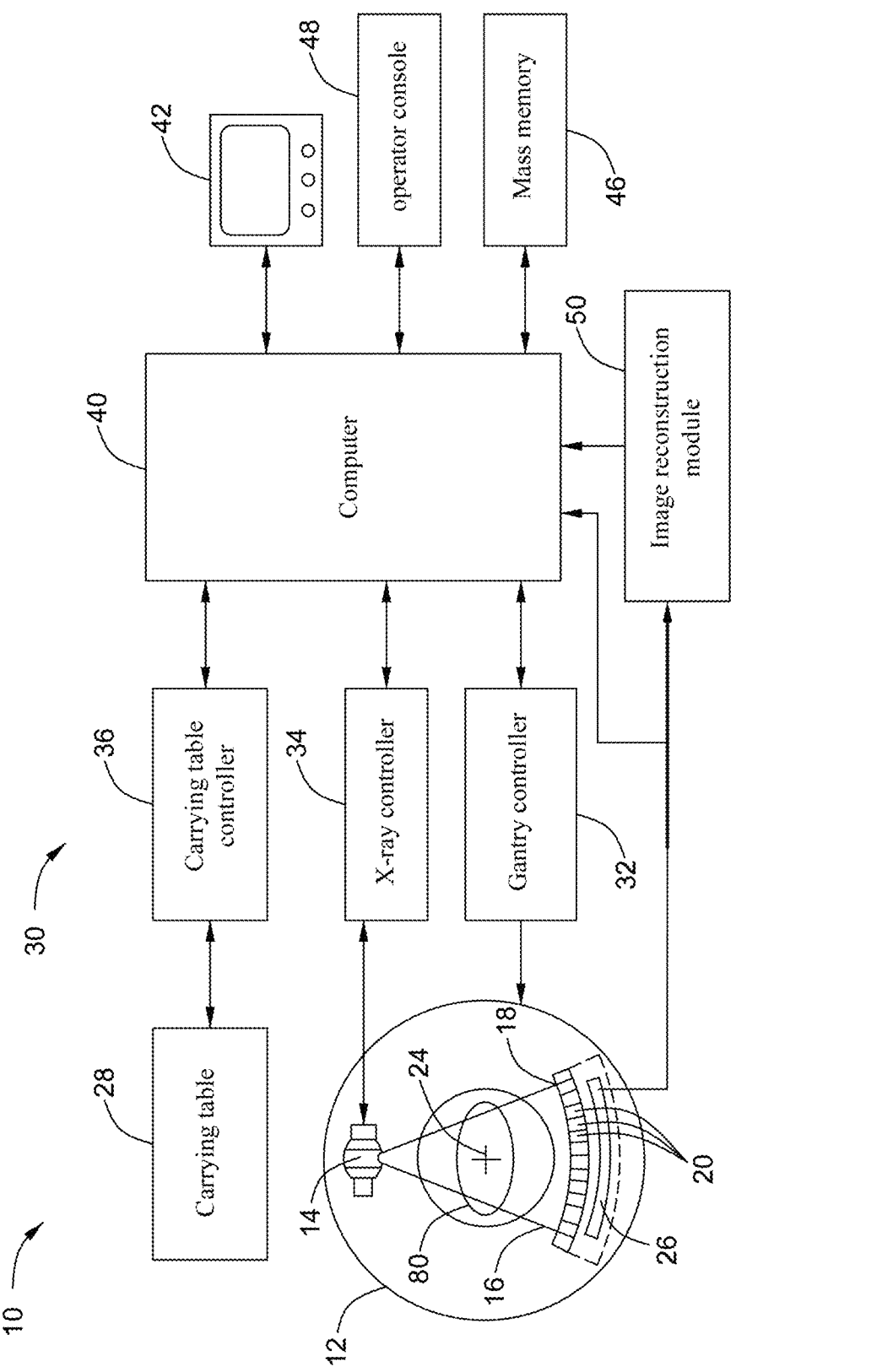
FIG. 1 is a schematic diagram of a CT system according to some embodiments of the present disclosure.

FIG. 1 is a schematic diagram of a CT system 10 according to some embodiments of the present disclosure. As shown in FIG. 1, the system 10 includes a gantry 12. An X-ray source 14 and a detector array 18 are disposed opposite to each other on the gantry 12. The detector array 18 is composed of a plurality of detectors 20 and a data acquisition system (DAS) 26. The DAS 26 is configured to convert sampled analog data of analog attenuation data received by the plurality of detectors 20 into digital signals for subsequent processing. In some embodiments, the system 10 is used for acquiring projection data of a subject under examination at different angles. Thus, components on the gantry 12 are used for rotating around a rotation center 24 to acquire projection data. During rotation, the X-ray radiation source 14 is configured to emit X-rays 16 that penetrate the subject under examination toward the detector array 18. The attenuated X-ray beam data is preprocessed and then used as projection data of a target volume of the subject. An image of the subject under examination may be reconstructed on the basis of the projection data. The reconstructed image may display internal features of the subject under examination. These features include, for example, the lesion, size, and shape of a body tissue structure. The rotation center 24 of the gantry also defines a center of a scanning field 80.

The system 10 further includes an image reconstruction module 50. As described above, the DAS 26 samples and digitizes the projection data acquired by the plurality of detectors 20. Next, the image reconstruction module 50 performs high-speed image reconstruction on the basis of the aforementioned sampled and digitized projection data. In some embodiments, the image reconstruction module 50 stores the reconstructed image in a storage apparatus or a mass memory 46. Or, the image reconstruction module 50 transmits the reconstructed image to a computer 40 to generate information for diagnosing and evaluating patients.

Although the image reconstruction module 50 is illustrated as a separate entity in FIG. 1, in some embodiments, the image reconstruction module 50 may form part of the computer 40. Or, the image reconstruction module 50 may not exist in the system 10, or the computer 40 may perform one or a plurality of functions of the image reconstruction module 50. Furthermore, the image reconstruction module 50 may be located at a local or remote location and may be connected to the system 10 using a wired or wireless communication network. In some embodiments, computing resources with a centralized cloud communication network may be used for the image reconstruction module 50.

In some embodiments, the system 10 includes a control mechanism 30. The control mechanism 30 may include an X-ray controller 34 configured to provide power and timing signals to the X-ray radiation source 14. The control mechanism 30 may further include a gantry controller 32 configured to control a rotational speed and/or position of the gantry 12 on the basis of imaging requirements. The control mechanism 30 may further include a carrying table controller 36 configured to drive a carrying table 28 to move to a suitable location so as to position the subject under examination in the gantry 12, thereby acquiring the projection data of the target volume of the subject under examination. Furthermore, the carrying table 28 includes a driving device, where the carrying table controller 36 may control the driving device to control the carrying table 28.

In some embodiments, the system 10 further includes the computer 40, where data sampled and digitized by the DAS 26 and/or an image reconstructed by the image reconstruction module 50 is transmitted to a computer or the computer 40 for processing. In some embodiments, the computer 40 stores the data and/or image in a storage apparatus such as a mass memory 46. The mass memory 46 may include a hard disk drive, a floppy disk drive, a CD-read/write (CD-R/W) drive, a digital versatile disc (DVD) drive, a flash drive, and/or a solid-state storage device. In some embodiments, the computer 40 transmits the reconstructed image and/or other information to a display 42, where the display 42 is communicatively connected to the computer 40 and/or the image reconstruction module 50. In some embodiments, the computer 40 may be connected to a local or remote display, printer, workstation and/or similar apparatus, for example, connected to such apparatuses of medical institutions or hospitals, or connected to a remote apparatus through one or a plurality of configured wires or a wireless communication network such as the Internet and/or a virtual private communication network.

Furthermore, the computer 40 may provide commands and parameters to the DAS 26 and the control mechanism 30 (including the gantry controller 32, the X-ray controller 34, and the carrying table controller 36) on the basis of user provision and/or system definition, so as to control system operation, for example, data acquisition and/or processing. In some embodiments, the computer 40 controls system operation on the basis of user input. For example, the computer 40 may receive user input such as commands, scanning protocols and/or scanning parameters, through an operator console 48 connected thereto. The operator console 48 may include a keyboard (not shown) and/or touch screen to allow a user to input/select commands, scanning protocols and/or scanning parameters. Although FIG. 1 exemplarily shows only one operator console 48, the computer 40 may be connected to more operating consoles, for example, for inputting or outputting system parameters, requesting medical examination, and/or viewing images.

In some embodiments, the system 10 may include or be connected to an image storage and transmission system (PACS) (not shown in the figure). In some embodiments, the PACS is further connected to a remote system such as a radiology information system, a hospital information system, and/or an internal or external communication network (not shown) to allow operators at different locations to provide commands and parameters and/or access image data.

The method or process described further below may be stored as executable instructions in a non-volatile memory in a computing apparatus of the system 10. For example, the computer 40 may include the executable instructions in the non-volatile memory, and may use the method described herein to automatically perform part or all of the scanning process, for example, select suitable protocols and determine suitable parameters. As another example, the image reconstruction module 50 may include the executable instructions in the non-volatile memory, and may use the method described herein to perform image reconstruction tasks.

The computer 40 may be configured and/or arranged for use in different manners. For example, in some implementations, a single computer 40 may be used. In other implementations, a plurality of computers 40 are configured to work together (for example, on the basis of distributed processing configuration) or separately, where each computer 40 is configured to handle specific aspects and/or functions, and/or process data for generating models used only for a specific medical imaging system 10. In some implementations, the computer 40 may be local (for example, in the same position as one or a plurality of medical imaging systems 10, for example, in the same facility and/or the same local communication network). In other implementations, the computer 40 may be remote and thus can only be accessed via a remote connection (for example, via the Internet or other available remote access technologies).

Figure 2:
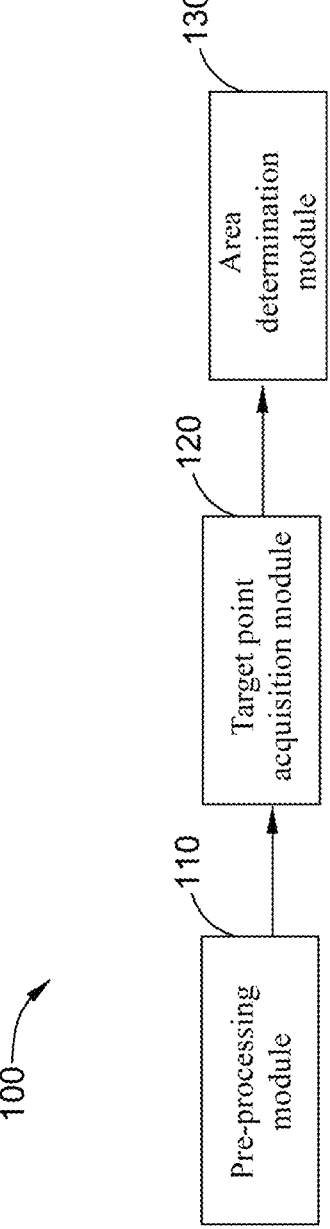
FIG. 2 is a schematic diagram of a target area determination device according to some embodiments of the present disclosure.
Figure 2:

FIG. 2 shows a target area determination device 100 in a medical imaging system according to some embodiments of the present disclosure. As shown in FIG. 2, the target area determination device 100 includes a pre-processing module 110, a target point acquisition module 120, and an area determination module 130. The pre-processing module 110 is configured to pre-process an original image to acquire a pre-processed medical image. The target point acquisition module 120 is configured to acquire a target point in the medical image, and to acquire a plurality of sectional images of the medical image according to the target point. The area determination module 130 is configured to acquire, on the basis of a first model, a target area corresponding to the target point in the plurality of sectional images.

In some embodiments, the target area determination device 100 may be part of the computer 40 (or processor) as shown in FIG. 1, or may perform storage and control in the form of a cloud device.

Specifically, the original image refers to an image obtained by means of reconstructing original data acquired after scanning. The original image may be directly acquired from a medical imaging system (for example, a CT system, an MRI system, a PET system, a PET-CT system, etc.), or may be acquired from a workstation or a PACS. In some non-limiting embodiments, the size of an image acquired from the CT system may be 512×512×n, where n is the number of layers scanned, e.g., 512×512×320.

The pre-processing includes at least one of resizing and pixel padding. Resizing refers to performing processing on pixel values, e.g., calculating an average pixel value of two or more pixel points. Pixel padding refers to padding certain pixel point locations with the pixel value of 0. The medical image of a preset size can be acquired by pre-processing the original image. For example, the preset size may be 256× 256×256. Performing pre-processing on the original image not only facilitates acquisition of the sectional images, determination of the target point, and determination of the target area performed subsequently, but also facilitates training and learning of a deep learning network.

In some embodiments, the pre-processing may also include conventional normalization processing and/or denoising, etc.

Although the preset size of the medical image mentioned above is 256*256*256, it should be understood by those skilled in the art that this size is exemplary only and that any other preset size may be used.

In some embodiments, the target point acquisition module 120 is capable of acquiring the target point in the medical image, wherein the target point in the medical image is a location center point of the original image. Specifically, for an original image having a size of 512×512×320, the coordinates of the location center point thereof are (256, 256, 160). After the original image is resized, the size of the image may be changed to 256×256×160 and the coordinates of the location center point at this moment are (128, 128, 80). Then pixel padding is performed on the resized image to obtain a medical image having a size of 256×256×256, but the coordinates of the target point in the medical image are still (128, 128, 80). That is, the target point in the medical image corresponds to the location center point of the original image rather than the location center point having the coordinates of (128, 128, 128) in the medical image.

If the location center point of the medical image is selected to be the target point, due to pixel padding, it is likely that the target point is not within the target area (e.g., within a heart area), or has a large offset from the center of the heart area. Consequently, the subsequent method steps of acquiring sectional images by means of the target point and determining a target area have the issue of large deviation from the beginning. Therefore, in order to enable the acquired target point to be as close to the center of the target area as possible, the location center point of the original image is mapped to the pre-processed medical image to be used as the target point, and the location center point of the medical image is not selected to be the target point, such that the target point is located within the target area and is as close to the center of the target area as possible.

Figure 3:
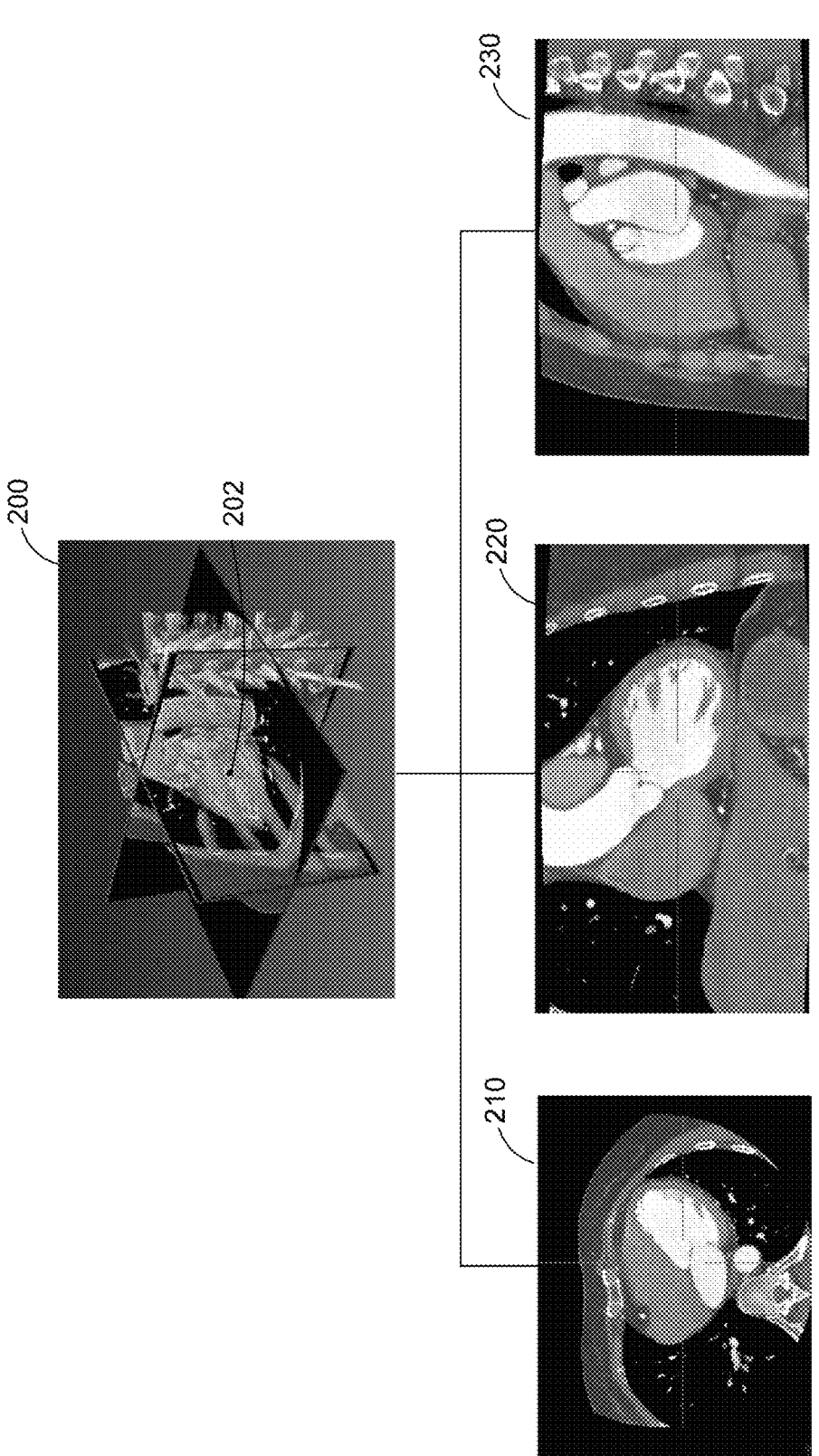
FIG. 3 is a schematic diagram of a medical image and a plurality of sectional images corresponding thereto.

FIG. 3 is a schematic diagram of a medical image 200 and a plurality of sectional images 210, 220, 230 corresponding thereto. As shown in FIG. 3, the target point acquisition module 120 may acquire the plurality of sectional images of the medical image 200 on the basis of an acquired target point 202. Specifically, the plurality of sectional images includes a coronal plane image 210, a sagittal plane image 220, and a transverse plane image 230. Specifically, a sagittal plane refers to an anatomical plane that divides the human body into left and right sides, a coronal plane refers to a sectional plane that vertically divides the human body into front and back portions along a long axis of the human body, and a transverse plane refers to a sectional plane that transects the human body into upper and lower portions in the anterior-posterior direction. Therefore, a plurality of sectional images can be obtained by means of the acquired target point and the three sectional planes passing through the target point.

By acquiring 2.5D images corresponding to the medical image, namely the plurality of sectional images including the transverse plane image, the coronal plane image and the sagittal plane image, and performing subsequent target area determination and/or other processing or operations on the basis of the 2.5D images, the problem of a heavy computation load resulting from computation and processing performed with respect to 3D images can be solved, and the problem of loss of information or details caused by using 2D images can also be solved. The present disclosure combines the advantages of 2D image processing and 3D image processing, and is capable of preserving more information and details while reducing the calculation load and complexity.

The area determination module 130 may determine the target area in the medical image, e.g., the heart area, on the basis of the first model. Specifically, the area determination module 130 includes a first training unit (not shown in the figure). The first training unit performs training and learning on the basis of training data to acquire the first model. The first model is a deep learning network model.

Specifically, the training data of the first model includes a first data set and a second data set. The first data set includes a plurality of sectional images having a preset target point. The second data set includes distances from the preset target point to respective edges of a reference target area in each sectional image. The preset target point includes an initial target point. The initial target point is a location center point of an original image. A reference target point is the center of the reference target area.

Specifically, for the first data set, an original image is pre-processed to acquire a medical image, and a location center point of the original image is mapped to the medical image (or the same pre-processing operation is carried out, but the location of pixel points remains unchanged). This point in the medical image is the initial target point. Then, corresponding sectional images are acquired on the basis of three sectional planes passing through the initial target point. An image set including a plurality of groups of sectional images containing an initial target point is the first data set.

In some embodiments, for the second data set, the reference target area is manually selected by a user or operator. The respective selection criteria for the reference target area may be different. For example, the distal end of a coronary artery may be preserved. In some non-limiting embodiments, the reference target area may be selected from the pre-processed medical image, and the target area (e.g., the heart area) is showed. The reference target point is the center point of the reference target area. In the process of acquiring the second data set, firstly, the reference target area is selected on the medical image; secondly, the corresponding sectional images are acquired via the initial target point, and each sectional image correspondingly shows a two-dimensional reference target area (or a cross-sectional view of the reference target area); and then, distances from the initial target point to respective edges of the two-dimensional reference target area are acquired. Therefore, the distances from the initial target point to the respective edges of the reference target area in each sectional image constitutes the second data set.

Figure 4:
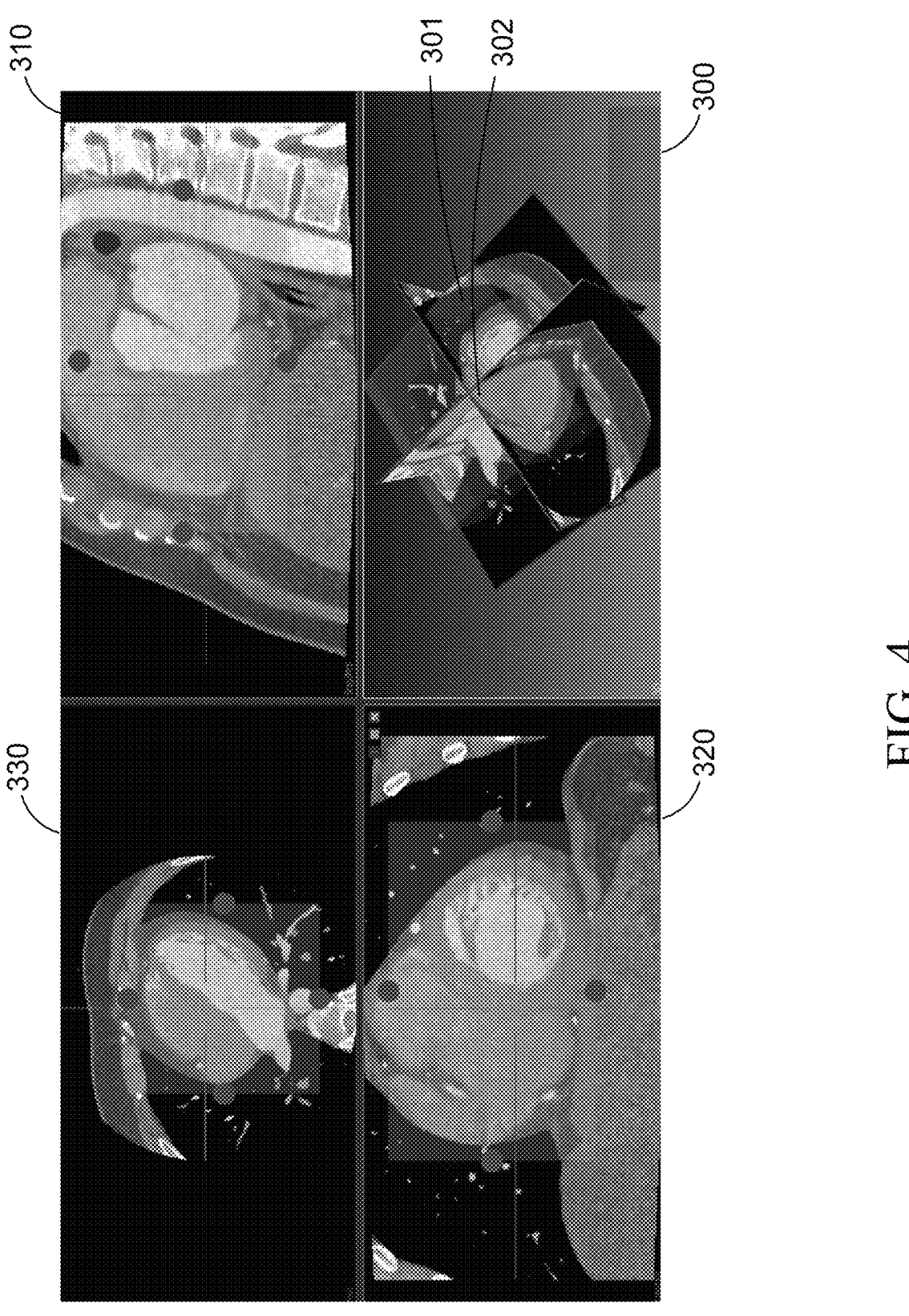
FIG. 4 is a schematic diagram of a reference target area in a medical image and sectional images.

FIG. 4 is a schematic diagram of a reference target area in a medical image and sectional images. As shown in FIG. 4, in a medical image 300, an area 301 shows a determined reference target area, and a plurality of sectional images 310, 320, and 330, each of which shows a corresponding reference target area, can be acquired via a center point 302 of the reference target area 301.

Specifically, the first model can be acquired by training an Inception-Resnet neural network model or other well-known models. Taking the first data set as a known input, and taking the second data set as an expected output, when training of the first model is completed, by inputting sectional images having a target point into the first model, distances from the target point to respective edges of a reference target area in each sectional image can be acquired, and a (three-dimensional) target area can be acquired on the basis of the distances.

Figure 5:
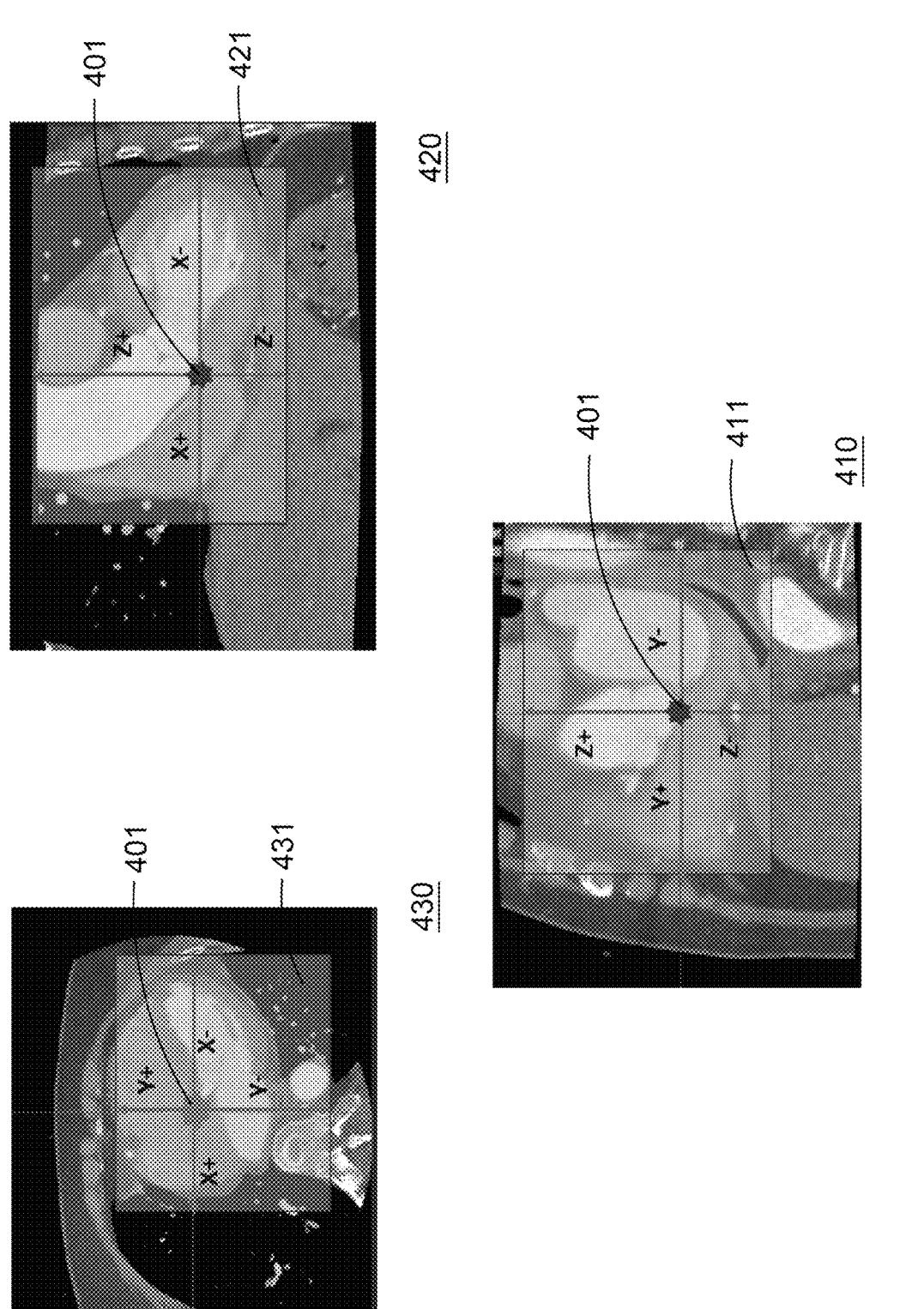
FIG. 5 is a schematic diagram of acquiring a target area by means of a first model.

FIG. 5 shows a schematic diagram of acquiring a target area via the first model. As shown in FIG. 5, by inputting a coronal plane image 410, a sagittal plane image 420 and a transverse plane image 430 having a target point 401 into the first model, distances (y+, y−, z+, z−) from the target point 401 to four edges of a reference target area 411 in the coronal plane image 410, distances (x+, x−, z+, z−) from the target point 401 to four edges of a reference target area 421 in the sagittal plane image 420, and distances (x+, x−, y+, y−) from the target point 401 to four edges of a reference target area 431 in the transverse plane image 430 can be acquired, wherein the reference target areas 411, 421 and 431 are two-dimensional areas of a three-dimensional reference target area on the coronal plane, sagittal plane, and transverse plane, respectively.

By acquiring the plurality of distances, a final three-dimensional target area can be acquired on the basis of the target point.

Although the figure only illustrates an example of acquiring the target (heart) area through a CT image, it should be understood by those of ordinary skill in the art that the target area is not limited to the heart area, and may include any other area, such as a brain structure or other tissue structure, and of course, is not limited to being acquired via a CT image either, or may also be acquired by performing processing on an MR image or a PET-CT image or other images.

Figure 6:
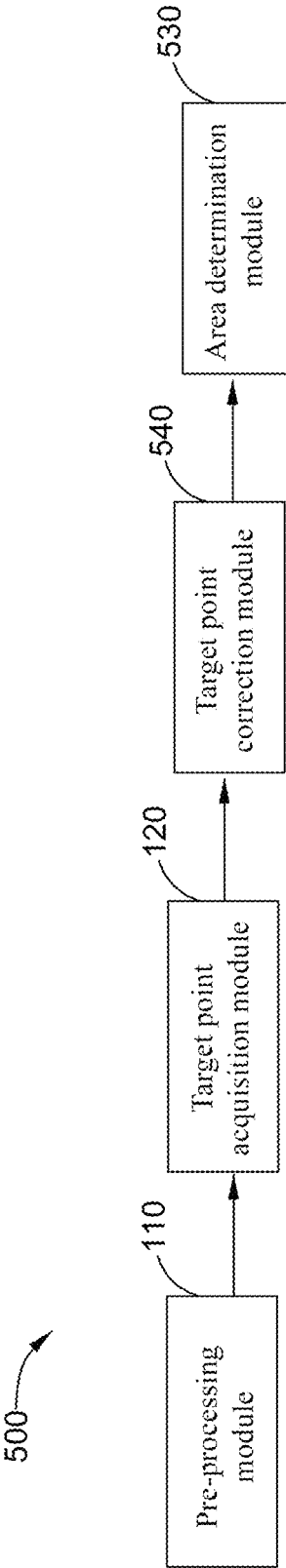
FIG. 6 is a schematic diagram of a target area determination device according to some other embodiments of the present disclosure.

FIG. 6 is a schematic diagram of a target area determination device 500 according to some other embodiments of the present disclosure. As shown in FIG. 6, unlike the target area determination device 200 shown in FIG. 2, the target area determination device 500 further includes a target point correction module 540. The target point correction module 540 corrects a target point in each sectional image to obtain a corrected target point, and acquires a plurality of corrected sectional images according to the corrected target point. Furthermore, an area determination module 530 may acquire a target area corresponding to the corrected target point in the plurality of corrected sectional images.

In some embodiments, the location of the target point acquired on the basis of the location center point of the original image may be too far from an actual target area or the center of the target area, resulting in large errors in the target area corresponding to the target point and acquired via the first model. Therefore, the target area determination device 500 may further correct the target point such that the corrected target point is located within the target area and is as close to the center as possible.

In some embodiments, the target point correction module 540 is further configured to acquire the corrected target point on the basis of a second model.

Training data of the second model includes a third data set and a fourth data set. The third data set includes a plurality of sectional images having an initial target point. The fourth data set includes an offset between the initial target point and a reference target point in each sectional image. The initial target point is a location center point of an original image. The reference target point is the center of a reference target area.

In some embodiments, the current third data set is the same as the first data set in the target area determination device 200, both including a plurality of sectional images having an initial target point.

The method of acquiring the fourth data set is similar to the method of acquiring the second data set in the target area determination device 200. Firstly, a reference target area is selected on a medical image; secondly, corresponding sectional images are acquired via the initial target point, and each sectional image correspondingly shows a two-dimensional reference target area (or a cross-sectional view of the reference target area); next, the center point of the two-dimensional reference target area, namely a reference target point, is determined, and the center of the two-dimensional reference target area is a mapped point of the center of a three-dimensional reference target on the sectional plane; and finally, the offset between the initial target point and the reference target point is acquired, and the offset is the distance between the two target points in two axial directions (parallel to two adjacent edges of the reference target area), e.g., the two axial distances of the two points on a coordinate axis. Thus, the offsets between the initial target point and the reference target points constitute the second data set.

Specifically, the second model may be an Inception-Resnet neural network model or other well-known models. Taking the third data set as a known input, and taking the fourth data set as an expected output, when training of the second model is completed, by inputting the sectional images having the target point into the second model, the offsets between the target point and the reference target points can be acquired, and the location of the corrected target point can be acquired on the basis of the distances.

In some embodiments, training data of the first model in the area determination module 530 at this moment includes a first data set and a second data set. The first data set includes a plurality of sectional images having a preset target point. The second data set includes distances from the preset target point to respective edges of a reference target area in each sectional image. The preset target point includes an offset target point. The offset target point is a target point having a preset offset from a reference target point. The reference target point is the center of the reference target area.

Specifically, with regard to the first data set, for the determined reference target area and the reference target point, some sectional images corresponding to the offset target point having the preset offset from the reference target point are manually selected to form the first data set.

The method of acquiring the second data set is similar to the method of acquiring the second data set in the target area determination device 200. Distances from the offset target point to respective edges of the reference target area are acquired in each sectional image.

When training of the first model is completed, by inputting the corrected sectional images having the corrected target point into the first model, distances from the corrected target point to respective edges of the reference target area can be acquired, and a target area can be acquired on the basis of the distances.

Although the target point is corrected by employing deep learning or artificial intelligence schemes as described above, it should be understood by those of ordinary skill in the art that the target point may be corrected using other means, and the target point may require no correction if the initial target point is located within the target area and close to the center.

The aforementioned first model and/or second model are/is a deep learning network. The deep learning network may include an input layer, an output layer, and a processing layer (or referred to as a hidden layer), wherein the input layer is configured to pre-process input data or image, for example, deaveraging, normalization, or dimensionality reduction, and the processing layer may include a convolutional layer configured to perform feature extraction, a batch normalization layer configured to perform standard normal distribution on the input, and an excitation layer configured to perform a nonlinear mapping on an output result of the convolutional layer. In addition, the deep learning network may further include a fully connected layer configured to output a corresponding offset.

Each convolutional layer includes several neurons, and the number of the neurons in each layer may be the same or set differently as required. On the basis of the first data set or the third data set (known input) and the second data set or the fourth data set (expected output), the number of processing layers in the network and the number of neurons in each processing layer are set, and a weight and/or a bias of the network is estimated (or adjusted or calibrated), so as to identify a mathematical relationship between the known input and the expected output and/or identify a mathematical relationship between the input and output of each layer.

Specifically, when the number of neurons in one of the layers is n, and values corresponding to the n neurons are $X_1$, $X_2$, . . . and $X_n$; the number of neurons in a next layer connected to the layer is m, and values corresponding to the m neurons are $Y_1$, $Y_2$, . . . and $Y_m$, the two adjacent layers may be represented as:

$$Y_j = f\left(\sum_{i=1}^{n} W_{ji}X_i + B_j\right)$$

wherein $X_i$ represents a value corresponding to the i-th neuron of a previous layer, $Y_j$ represents a value corresponding to the j-th neuron of a next layer, $W_{ji}$ represents a weight, and $B_j$ represents a bias. In some embodiments, the function $f$ is a rectified linear function.

Thus, by adjusting the weight $W_{ji}$ and/or the bias $B_j$, the mathematical relationship between the input and output of each layer can be identified, so that a loss function converges, so as to obtain the aforementioned first model and/or second model through training.

In one embodiment, although the configuration of the deep learning network is guided by dimensions such as prior knowledge, input, and output of an estimation problem, optimal approximation of required output data is implemented depending on or exclusively according to input data.

In various alternative implementations, clear meaning may be assigned to some data representations in the deep learning network using some aspects and/or features of data, an imaging geometry, a reconstruction algorithm, or the like, which helps to speed up training. This creates an opportunity to separately train (or pre-train) or define some layers in the deep learning network.

In some embodiments, the aforementioned trained network is obtained on the basis of training by a training module on an external carrier (for example, a device outside the medical imaging system). In some embodiments, the training system may include a first module configured to store a training data set, a second module configured to perform training and/or update on the basis of a model, and a communication network configured to connect the first module and the second module. In some embodiments, the first module includes a first processing unit and a first storage unit, where the first storage unit is configured to store the training data set, and the first processing unit is configured to receive a relevant instruction (for example, acquiring a training data set) and send the training data set according to the instruction. In addition, the second module includes a second processing unit and a second storage unit, where the second storage unit is configured to store a training model, and the second processing unit is configured to receive a relevant instruction and perform training and/or update of the network. In some other embodiments, the training data set may further be stored in the second storage unit of the second module, and the training system may not include the first module. In some embodiments, the communication network may include various connection types, such as wired or wireless communication links, or fiber-optic cables.

Once data (for example, a trained model) is generated and/or configured, the data can be replicated and/or loaded into the medical imaging system 10, which may be accomplished in a different manner. For example, models may be loaded via a directional connection or link between the medical imaging system 10 and the computer 40. In this regard, communication between different elements may be accomplished using an available wired and/or wireless connection and/or on the basis of any suitable communication (and/or network) standard or protocol. Alternatively or additionally, the data may be indirectly loaded into the medical imaging system 10. For example, the data may be stored in a suitable machine-readable medium (for example, a flash memory card), and then the medium is used to load the data into the medical imaging system 10 (for example, by a user or an authorized person of the system on site); or the data may be downloaded to an electronic apparatus (for example, a notebook computer) capable of local communication, and then the apparatus is used on site (for example, by a user or an authorized person of the system) to upload the data to the medical imaging system 10 via a direct connection (for example, a USB connector).

As discussed herein, the deep learning technology (also referred to as deep machine learning, hierarchical learning, deep structured learning, or the like) employs an artificial neural network for learning. The deep learning method is characterized by using one or a plurality of network architectures to extract or simulate data of interest. The deep learning method may be implemented using one or a plurality of processing layers (for example, an input layer, an output layer, a convolutional layer, a normalization layer, or a sampling layer, where processing layers of different numbers and functions may exist according to different deep network models), where the configuration and number of the layers allow a deep network to process complex information extraction and modeling tasks. Specific parameters (or referred to as "weight" or "bias") of the network are usually estimated through a so-called learning process (or training process). The learned or trained parameters usually result in (or output) a network corresponding to layers of different levels, so that extraction or simulation of different aspects of initial data or the output of a previous layer usually may represent the hierarchical structure or concatenation of layers. During image processing or reconstruction, this may be represented as different layers with respect to different feature levels in the data. Thus, processing may be performed layer by layer. That is, "simple" features may be extracted from input data for an earlier or higher-level layer, and then these simple features are combined into a layer exhibiting features of higher complexity. In practice, each layer (or more specifically, each "neuron" in each layer) may process input data as output data for representation using one or a plurality of linear and/or non-linear transformations (so-called activation functions). The number of the plurality of "neurons" may be constant among the plurality of layers or may vary from layer to layer. As discussed herein, as part of initial training of a deep learning process to solve a specific problem, a training data set includes a known input value (for example, a sample image or a pixel matrix of the image subjected to coordinate transformation) and an expected (target) output value (for example, an image or an identification and determination result) finally outputted in the deep learning process. In this manner, a deep learning algorithm can process the training data set (in a supervised or guided manner or an unsupervised or unguided manner) until a mathematical relationship between a known input and an expected output is identified and/or a mathematical relationship between the input and output of each layer is identified and represented. In the learning process, (part of) input data is usually used, and a network output is created for the input data. Afterwards, the created network output is compared with the expected output of the data set, and then a difference between the created and expected outputs is used to iteratively update network parameters (weight and/or bias). A stochastic gradient descent (SGD) method may usually be used to update network parameters. However, those skilled in the art should understand that other methods known in the art may also be used to update network parameters. Similarly, a separate validation data set may be used to validate a trained network, where both a known input and an expected output are known. The known input is provided to the trained network so that a network output can be obtained, and then the network output is compared with the (known) expected output to validate prior training and/or prevent excessive training.

In some embodiments, the medical imaging system (or a computer therein) includes a processor. The processor can be used to perform the method including pre-processing an original image to obtain a pre-processed medical image; acquiring a target point in the medical image, and acquiring a plurality of sectional images of the medical image according to the target point; and acquiring, on the basis of a first model, a target area corresponding to the target point in the plurality of sectional images.

Figure 7:
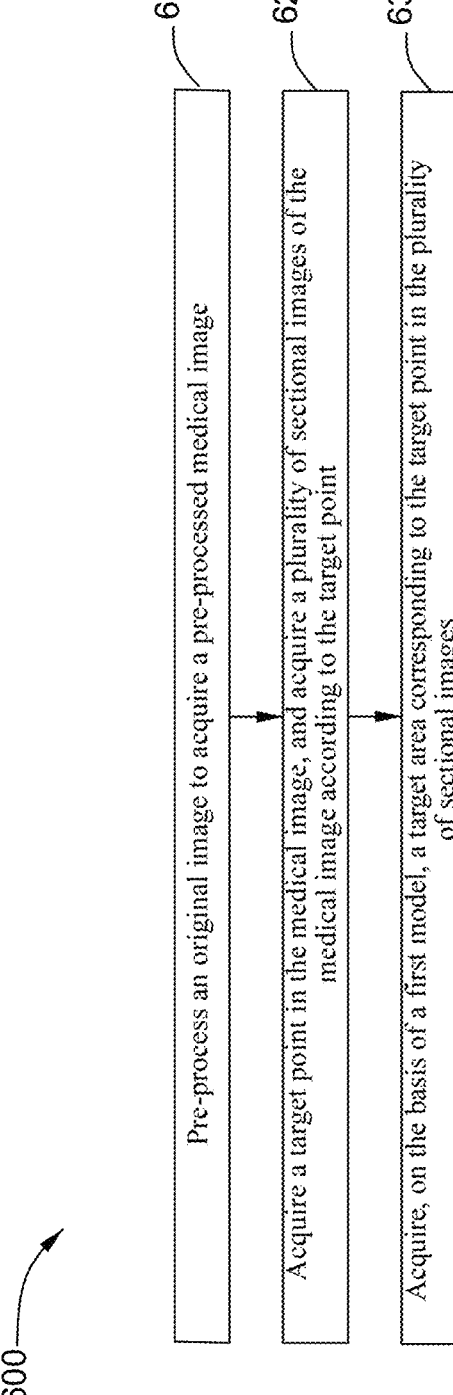
FIG. 7 is a flowchart of a target area determination method according to some embodiments of the present disclosure.

FIG. 7 is a flowchart of a target area determination method 600 according to some embodiments of the present disclosure. As shown in FIG. 7, the target area determination method 600 includes step 610, step 620 and step 630.

In step 610, the original image is pre-processed to obtain a pre-processed medical image.

Specifically, the original image refers to an image obtained by means of reconstructing original data acquired after scanning. The original image may be directly acquired from a medical imaging system (e.g., a CT system, an MRI system, a PET system, and a PET-CT system), or may be acquired from a workstation or a PACS. In some non-limiting embodiments, the size of the image acquired from the CT system may be 512×512×n, wherein n is the number of layers scanned, e.g., 512×512×320.

The pre-processing includes at least one of resizing and pixel padding. Resizing refers to continuously performing processing on pixel values. Pixel padding refers to padding certain pixel point locations with the pixel value of 0. By pre-processing the original image, a medical image of a preset size can be acquired. Performing pre-processing on the original image not only facilitates acquisition of sectional images, determination of a target point, and determination of a target area performed subsequently, but also facilitates training and learning of a deep learning network.

In step 620, a target point in the medical image is acquired, and a plurality of sectional images of the medical image are acquired according to the target point.

The target point in the medical image is a location center point of the original image. For example, for an original image having a size of 512×512×320, the coordinates of the location center point thereof are (256, 256, 160). After the original image is resized, the size of the image may be changed to 256×256×160, and the coordinates of the location center point at this moment are (128, 128, 80). Then pixel padding is performed on the resized image to obtain a medical image (namely the pre-processed medical image) having a size of 256×256×256, and the location of the target point in the medical image corresponds to the location center point having the coordinates of (128, 128, 80) of the original image.

The plurality of sectional images includes a transverse plane image, a coronal plane image and a sagittal plane image. The plurality of sectional images can be obtained on the basis of the acquired target point and three sectional planes passing through the target point.

By acquiring 2.5D images corresponding to the medical image, namely the plurality of sectional images, and performing subsequent target area determination and/or other processing or operations on the basis of the 2.5D images, the problem of a heavy computation load resulting from computation and processing performed with respect to 3D images can be solved, and the problem of loss of information or details caused by using 2D images can also be solved. The present disclosure combines the advantages of 2D image processing and 3D image processing, and is capable of preserving more information and details while reducing the computation load and complexity.

In step 630, a target area corresponding to the target point in the plurality of sectional images is acquired on the basis of a first model.

Specifically, step 630 further includes: inputting the plurality of sectional images containing the target point into the first model and outputting distances from the target point to respective edges of a reference target area in each sectional image, and acquiring a target area on the basis of the distances.

Training data of the first model includes a first data set and a second data set. The first data set includes a plurality of sectional images having a preset target point. The second data set includes distances from the preset target point to the respective edges of the reference target area in each sectional image. The preset target point includes an initial target point.

The initial target point is a location center point of an original image. A reference target point is the center of the reference target area.

Specifically, the first model may be an Inception-Resnet neural network model or other well-known models. Taking the first data set as a known input, and taking the second data set as an expected output, when training of the first model is completed, by inputting the sectional images having the target point into the first model, the distances from the target point to the respective edges of the reference target area can be acquired, and a target area can be acquired on the basis of the distances.

For example, by acquiring distances (y+, y−, z+, z−) from the target point to four edges of the reference target area on a coronal plane image, distances (x+, x−, z+, z−) from the target point to four edges of the reference target area on the sagittal plane image, and distances (x+, x−, y+, y−) from the target point to four edges of the reference target area on the transverse plane image, the location of the entire target area can be acquired.

FIG. 8 is a flowchart of a target area determination method 700 according to some other embodiments of the present disclosure. Different from the target area determination method 600 shown in FIG. 7, the target area determination method 700 further includes step 740.

In step 740, the target point in each sectional image is corrected to acquire a corrected target point, and a plurality of corrected sectional images are acquired according to the corrected target point.

Specifically, correcting the target point in each sectional image includes: acquiring a corrected target point on the basis of a second model.

Training data of the second model includes a third data set and a fourth data set. The third data set includes a plurality of sectional images having an initial target point. The fourth data set includes an offset between the initial target point and a reference target point in each sectional image. The initial target point is a location center point of an original image. The reference target point is the center of the reference target area.

Specifically, the second model may be obtained by training an Inception-Resnet neural network model or other well-known models. Taking the third data set as a known input, and taking the fourth data set as an expected output, when training of the second model is completed, by inputting the sectional images having the target point into the second model, offsets between the target point and the reference target points can be acquired, and a corrected target point can be acquired on the basis of the offsets.

And in step 730, a target area corresponding to the corrected target point in the plurality of corrected sectional images is acquired on the basis of a first model.

Training data of the first model at this moment includes a first data set and a second data set. The first data set includes a plurality of sectional images having a preset target point. The second data set includes a plurality of sectional images having reference target areas. The preset target point includes an offset target point. The offset target point is a target point having a preset offset from a reference target point. The reference target point is the center of the reference target area.

When training of the first model is completed, by inputting the corrected sectional images having the corrected target point into the first model, distances from the corrected target point to the respective edges of the reference target area can be acquired, and a target area can be acquired on the basis of the distances.

According to the target area determination method provided by the present disclosure, the use of sectional images (a transverse plane image, a coronal plane image and a sagittal plane image) to determine a target area can effectively prevent the defects of 3D image processing and 2D image processing while combining advantages of the same, thereby preserving details in the image while reducing the computation complexity and processing complexity. Moreover, a deep learning network is used to determine a target area for sectional images, such that a user does not need to manually perform determination by using other means, thereby improving operation efficiency and user experience. Furthermore, correcting an initial target point before determination of a target area ensures that the target point is located within the target area and is as close to the center of the target area as possible, and this provides a basis for accurately determining the target area subsequently.

The present disclosure may further provide a non-transitory computer-readable storage medium for storing an instruction set and/or a computer program. When executed by a computer, the instruction set and/or computer program causes the computer to perform the target area determination method. The computer executing the instruction set and/or computer program may be a computer of a medical imaging system, or may be other devices/modules of the medical imaging system. In one embodiment, the instruction set and/or computer program may be programmed into a processor/controller of the computer.

Specifically, when executed by the computer, the instruction set and/or computer program causes the computer to pre-process an original image to acquire a pre-processed medical image, acquire a target point in the medical image, and acquire a plurality of sectional images of the medical image according to the target point, and acquire, on the basis of a first model, a target area corresponding to the target point in the plurality of sectional images.

The instructions described above may be combined into one instruction for execution, and any of the instructions may also be split into a plurality of instructions for execution. Moreover, the present disclosure is not limited to the instruction execution order described above.

As used herein, the term "computer" may include any processor-based or microprocessor-based system that includes a system using a microcontroller, a reduced instruction set computer (RISC), an application specific integrated circuit (ASIC), a logic circuit, and any other circuit or processor capable of performing the functions described herein. The examples above are exemplary only and are not intended to limit the definition and/or meaning of the term "computer" in any way.

The instruction set may include various commands used to instruct the computer serving as a processing machine or the processor to perform specific operations, e.g., methods and processes of various embodiments. The instruction set may be in the form of a software program that may form part of one or more tangible, non-transitory computer readable media. The software may be in various forms of, e.g., system software or application software. Furthermore, the software may be in the form of a standalone program or a collection of modules, a program module within a larger program, or part of a program module. The software may also include modular programming in the form of object-oriented programming. Processing of the input data by the processing machine may be in response to an operator command, or in response to a previous processing result, or in response to a request made by another processing machine.

Some exemplary embodiments have been described above, however, it should be understood that various modifications may be made. For example, suitable results can be achieved if the described techniques are performed in different orders and/or if components in the described systems, architectures, devices, or circuits are combined in different ways and/or replaced or supplemented by additional components or equivalents thereof. Accordingly, other implementations also fall within the protection scope of the claims.

What is claimed is:

1. A target area determination method for a medical image, comprising:

pre-processing an original volumetric image to generate a standardized medical image, wherein the pre-processing includes at least one of resizing, pixel padding, normalization, or denoising;

acquiring a target point in the medical image, the target point corresponding to a mapped location center of the original volumetric image;

acquiring a plurality of sectional images of the medical image based on the target point, wherein each of the sectional images corresponds to a sectional plane passing through the target point, wherein the sectional plane includes at least one of a transverse plane, a coronal plane, and a sagittal plane;

correcting the target point in each sectional image using a first deep learning model trained on offset data to acquire a corrected target point;

acquiring a plurality of corrected sectional images according to the corrected target point; and acquiring, based on a second deep learning model trained on distance data representing spatial offsets from the corrected target point to anatomical boundaries, a target area corresponding to the target point in the plurality of corrected sectional images, wherein the target area is determined based on output distances from the target point to respective edges of a reference target area.

2. The target area determination method according to claim 1, wherein the pre-processing comprises at least one of resizing and pixel padding.

3. The target area determination method according to claim 1, wherein the target point in the medical image is a location center point of the original image.

4. The target area determination method according to claim 1, wherein the plurality of sectional images include a transverse plane image, a coronal plane image and a sagittal plane image.

5. The target area determination method according to claim 1, wherein training data of the second model includes a first data set and a second data set, wherein the first data set includes a plurality of sectional images having a preset target point, the second data set includes distances from the preset target point to respective edges of a reference target area in each sectional image, where the preset target point includes an initial target point or an offset target point, the initial target point is a location center point of an original image, the offset target point is a target point having a preset offset from a reference target point, and the reference target point is the center of the reference target area.

6. The target area determination method according to claim 5, wherein the acquiring the target area corresponding to the target point in the plurality of sectional images includes:

inputting the plurality of sectional images containing the target point into the second model, and outputting distances from the target point to respective edges of a reference target area in each sectional image; and acquiring the target area based on the distances.

7. The target area determination method according to claim 1, wherein the correcting the target point in each sectional image includes acquiring the corrected target point based on the first model.

8. The target area determination method according to claim 7, wherein training data of the first model includes a third data set and a fourth data set, wherein the third data set includes a plurality of sectional images having an initial target point, and the fourth data set comprises an offset between the initial target point and a reference target point in each sectional image, where the initial target point is a location center point of an original image, and the reference target point is the center of a reference target area.

9. A medical imaging system, comprising a target area determination device, the target area determination device comprising:

a pre-processing module configured to pre-process an original volumetric image to generate a pre-processed medical image, wherein the pre-processing includes at least one of resizing, pixel padding, normalization, or denoising;

a target point acquisition module configured to acquire a target point corresponding to a mapped location center of the original volumetric image, and to acquire a plurality of sectional images of the medical image based on the target point, wherein each of the sectional images corresponds to a sectional plane passing through the target point;

a target point correction module configured to correct the target point in each sectional image using a first deep learning model trained on offset data representing spatial deviations from anatomical boundaries, to acquire a corrected target point, and to acquire a plurality of corrected sectional images according to the corrected target point; and an area determination module configured to acquire, based on a second deep learning model trained on distance data representing spatial offsets from the corrected target point of anatomical boundaries, a target area corresponding to the target point in the plurality of sectional images, wherein the target area is determined based on output distances from the target point to respective edges of a reference target area.

10. The medical imaging system according to claim 9, wherein the target point in the medical image is a location center point of the original image.

11. The medical imaging system according to claim 9, wherein the area determination module is configured to acquire the target area corresponding to the corrected target point in the plurality of corrected sectional images.

12. The target area determination method according to claim 1, wherein the target area is a heart.

* * * * *